US006855347B2

(12) United States Patent
Rao et al.

(10) Patent No.: US 6,855,347 B2
(45) Date of Patent: Feb. 15, 2005

(54) COMPOSITION FOR TREATING GASTRIC ULCER AND A PROCESS FOR PREPARING THE SAME

(75) Inventors: Janaswamy Madhusudana Rao, Hyderabad (IN); Upparapalli Sampathkumar, Hyderabad (IN); Boggavarapu Subrahmanya Sastry, Hyderabad (IN); Jhillu Singh Yadav, Hyderabad (IN); Kondapuram Vijaya Raghavan, Hyderabad (IN); Gautam Palit, Lucknow (IN); Deepak Rai, Lucknow (IN); Panniyampally Madhavankutty Varier, Kerala (IN); Trikovil Sankaran Muraleedharan, Kerala (IN); Kollath Muraleedharan, Kerala (IN)

(73) Assignee: Council of Scientific and Industrial Research, New Delhi (IN)

( * ) Notice: Subject to any disclaimer, the term of this patent is extended or adjusted under 35 U.S.C. 154(b) by 80 days.

(21) Appl. No.: 10/103,738

(22) Filed: Mar. 25, 2002

(65) Prior Publication Data

US 2003/0180398 A1 Sep. 25, 2003

(51) Int. Cl.$^7$ .......................... A61K 35/78; A01N 65/00

(52) U.S. Cl. ...................... 424/734; 424/725; 424/756; 424/761; 424/763; 424/765; 424/766; 424/769; 424/773; 424/774; 424/775; 424/776; 424/777; 424/778; 424/779; 514/925; 514/926; 514/927

(58) Field of Search ................................. 424/725, 734, 424/756, 761, 763, 765, 766, 769, 773–779; 514/925–927

(56) References Cited

U.S. PATENT DOCUMENTS

2003/0185913 A1 * 10/2003 Pushpangadan et al. ..... 424/739

FOREIGN PATENT DOCUMENTS

IN             174417      * 3/1994

* cited by examiner

*Primary Examiner*—John Pak
(74) *Attorney, Agent, or Firm*—Piper Rudnick LLP; Steven B. Kelber

(57) ABSTRACT

The present invention relates to a novel synergistic herbal composition for the treatment of gastric ulcer, a method for preparing said synergistic herbal composition and a process for the treatment of gastric ulcer using said composition and more particularly, the present invention relates to a novel synergistic herbal composition which is effective against pyloric ligation induced ulcer model and histamine induced ulcer model.

15 Claims, No Drawings

COMPOSITION FOR TREATING GASTRIC ULCER AND A PROCESS FOR PREPARING THE SAME

FIELD OF THE INVENTION

The present invention relates to a novel synergistic herbal composition for the treatment of gastric ulcer. More particularly, the present invention relates to a novel synergistic herbal composition which is effective against pyloric ligation induced ulcer model and histamine induced ulcer model. The present invention also relates to a method for the preparation of the composition. The present invention further relates to a process for the treatment of gastric ulcer using the composition.

BACKGROUND OF THE TECHNOLOGY

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric or duodenal acid secretion. Accordingly it is important to suppress the acid secretion in order to prevent ulcer formation and to cure it.

On the other hand it has been considered that *Helicobacter pylori*, which is a rod normally existing in stomach, generates ammonia due to its strong urease activity, thereby inducing ulcer. Since it persistently lives within mucus and mucosa, it becomes the greatest cause for recurrence of ulcer. Accordingly, it has been considered that the recurrence of ulcer can be prevented if this bacterium is sterilized.

A reference may be made to K. M. Nadkarni in Indian Materia Medica (1976) Vol. 1, p1287, published by Popular Prakashan Pvt. Ltd., Mumbai and K. R. Kirtikar in Indian Medicinal Plants (1975) Vol. 1, p 608 published by Bishen Singh Mahendrapal Singh, Dehradun for the medicinal properties of *Blechnum orintale*.

A reference may be made to P. K. Warrier in Indian Medicinal Plants—A compendium of 500 species (1994–1996) Vol. 5, p 396, and The Wealth of India (1950–1980), Vol.10 p. 556 published by Council of Scientific and Industrial Research for the various medicinal properties of *Vitis vinifera*.

A reference may be made to K. Narayana Iyer and M. Kolammal in Pharmacognosy of Ayurvedic Drugs (1963) Vol.2, p. 80, published by Department of Pharmacognosy, University of Kerala, Trivandrum and The Wealth of India (1950–1980) Vol. 1, p. 34, published by Council of Scientific and Industrial Research for the various medicinal properties of *Aegle marmelos*.

A reference may be made to K. M. Nadkarni in Indian Materia Medica (1976) Vol. 1, p. 1239–94, published by Popular Prakashan Pvt. Ltd., Mumbai; K. R. Kirtikar in Indian Medicinal Plants (1975) Vol. 2, p 1776 published by Bishen Singh Mahendrapal Singh, Dehradun; P. K. Warrier in Indian Medicinal Plants—A compendium of 500 species (1994–1996) Vol. 5, p 409; K. Narayana Iyer and M. Kolammal in Pharmacognosy of Ayurvedic Drugs (1963) Vol.8, p. 34, published by Department of Pharmacognosy, University of Kerala, Trivandrum, The Wealth of India (1950–1980) Vol. 10, p. 585, published by Council of Scientific and Industrial Research and S. S. Handa in Indian Herbal Pharmacopoeia (1998), Vol. 1, p.171, published by Regional Research Laboratory, Jammu and IDMA, Mumbai for the various medicinal properties of *Withania somnifra*.

A reference may be made to K. M. Nadkarni in Indian Materia Medica (1976) Vol. 1, p 536, published by Popular Prakashan Pvt. Ltd., Mumbai; K. R. Kirtikar in Indian Medicinal Plants (1975) Vol. 1, p 997 published by Bishen Singh Mahendrapal Singh, Dehradun; P. K. Warrier in Indian Medicinal Plants—A compendium of 500 species (1994–1996) Vol. 3, p. 327–29, and The Wealth of India (1950–1980) Vol. 4, p. 19, published by Council of Scientific and Industrial Research of the various medicinal properties of *Feronia elephantum*.

A reference may be made to K. M. Nadkarni in Indian Materia Medica (1976) Vol. 1, p1031, published by Popular Prakashan Pvt. Ltd., Mumbai; P. K. Warrier in Indian Medicinal Plants—A compendium of 500 species (1994–1996) Vol. 4, p 396, and in Illustrated manual of herbal drugs used in Ayurveda (1996) by Y. K. Sarin p.218 for the various medicinal properties of *Punica grantum*.

A reference may be made to K. M. Nadkarni in Indian Materia Medica (1976) Vol. 1, p1309, published by Popular Prakashan Pvt. Ltd., Mumbai; K. R. Kirtikar in Indian Medicinal Plants (1975) Vol. 4, p 2436 published by Bishen Singh Mahendrapal Singh, Dehradun; P. K. Warrier in Indian Medicinal Plants—A compendium of 500 species (1994–1996) Vol. 5, p. 431, published by orient Longman, Chennai, and The Ayurvedic Pharmacopoeia of India (1986), Vol. 1, p. 104, published by Ministry of Health and Family Welfare, India for the various medicinal properties of *Ziniber officnale*.

A reference may be made to K. M. Nadkarni in Indian Materia Medica (1976) Vol. 1, p. 478, published by Popular Prakashan Pvt. Ltd., Mumbai; P. K. Warrier in Indian Medicinal Plants—A compendium of 500 species (1994–1996) Vol. 2, p. 368, published by orient Longman, Chennai; Medicinal plants of India (1987) by G. V. Satyavati Vol. 2 p.429 published by Indian Council of Medical Research; The Wealth of India (1950–1980) Vol. 8, p. 98, published by Council of Scientific and Industrial Research, and Y. K. Sarin in Illustrated manual of herbal drugs used in Ayurveda (1996), p. 268 for the various medicinal properties of *Piper nigrum*.

A reference may be made to K. M. Nadkarni in Indian Materia Medica (1976) Vol. 1, p. 966, published by Popular Prakashan Pvt. Ltd., Mumbai; P. K. Warrier in Indian Medicinal Plants—A compendium of 500 species (1994–1996) Vol. 4, p. 290, published by orient Longman, Chennai; K. Narayana Iyer and M. Kolammal in Pharmacognosy of Ayurvedic Drugs (1963) Vol.9, p. 49, published by Department of Pharmacognosy, University of Kerala, Trivandrum, and The Wealth of India (1950–1980) Vol. 8, p. 98, published by Council of Scientific and Industrial Research for the various medicinal properties of *Piper longum*.

A reference may be made to K. R. Kirtikar in Indian Medicinal Plants (1975) Vol. 1, p536–540 published by Bishen Singh Mahendrapal Singh, Dehradun; P. K. Warrier in Indian Medicinal Plants—A compendium of 500 species (1994–1996) Vol. 1, p. 203–5, published by orient Longman, and K. Narayana Iyer and M. Kolammal in Pharmacognosy of Ayurvedic Drugs (1963) Vol.3, p. 23, published by Department of Pharmacognosy, University of Kerala, Trivandrum for the various medicinal properties of *Azadirachta indica*.

The composition of the present invention should not be treated as an obvious one as none of the citations are able to provide all the advantages of the present invention. .

Objects of the Invention

The main object of the present invention is to provide a novel synergistic herbal composition for the treatment of gastric ulcer.

Yet another object of the present invention is to provide a process for the preparation of the composition.

Still another object of the present invention is to provide a method for the treatment of gastric ulcer using the composition.

SUMMARY OF THE INVENTION

The present invention provides a novel synergistic herbal composition for the treatment of gastric ulcer. More particularly, the present invention relates to a novel synergistic herbal composition which is effective against pyloric ligation induced ulcer model and histamine induced ulcer model. Also, the present invention provides a process for the preparation of the composition. The present invention further provides a method for the treatment of gastric ulcer using said composition.

DETAILED DESCRIPTION OF THE PRESENT INVENTION

In accordance with the first object of the present invention, there is provided a novel synergistic herbal composition for the treatment of gastric ulcer, said composition comprises an extract essentially obtained from one or more parts of *Aegle marmelos* and *Withania somnifra* and optionally from one or more parts of *Blechnum orintale, Vitis vinifera, Feronia elephantum, Punica grantum, Ziniber officnale, Piper nigrum, Piper longum* and *Azadirachta indica* along with one or more pharmaceutically acceptable additives/carriers.

More particularly, the present invention provides a novel synergistic herbal composition for the treatment of gastric ulcer, said composition essentially comprises 4–10% by wt. of an extract from *Aegle marmelos* and 4–11% by wt. of an extract from *Withania somnifra* and optionally comprises 5–8% by wt. of an extract from *Blechnum orintale*, 5–11% by wt. of an extract from *Vitis vinifera*, 5–9% by wt. of an extract from *Feronia elephantum*, 8–11% by wt. of an extract from *Punica grantum*, 4–9% by wt. of an extract from *Ziniber officnale*, 2–11% by wt. of an extract from *Piper nigrum*, 8–12% by wt. of an extract from *Piper longum* and 2–11% by wt. of an extract from *Azadirachta indica* along with one or more pharmaceutically acceptable additives/carriers.

In an embodiment of the present invention, the extract is an aqueous extract.

In another embodiment of the present invention, the plant part of *Aegle marmelos, Withania somnifra* and *Blechnum orintale* is root.

In still another embodiment of the present invention, the plant part of *Vitis vinifera, Feronia elephantum, Piper nigrum* and *Piper longum* is fruit.

In yet another embodiment of the present invention, the plant part of *Punica grantum* is fruit rind.

In one more embodiment of the present invention, the plant part of *Ziniber officnale* is rhizome.

In one another embodiment of the present invention, the plant part of *Azadirachta indica* is bark.

In accordance with the second object of the present invention, there is provided a process for the preparation of the novel synergistic herbal composition for the treatment of gastric ulcer, said process comprising obtaining an extract essentially from one or more parts of *Aegle marmelos* and *Withania somnifra* and optionally from one or more parts of *Blechnum orintale, Vitis vinifera, Feronia elephantum, Punica grantum, Ziniber officnale, Piper nigrum, Piper longum* and *Azadirachta indica* and mixing them with one or more pharmaceutically acceptable additives/carriers.

In an embodiment of the present invention, said process extract is obtained by grinding 4–10% by wt. of an extract from *Aegle marmelos* and 4–11% by wt. of an extract from *Withania somnifra* and optionally 5–8% by wt. of an extract from *Blechnum orintale*, 5–11% by wt. of an extract from *Vitis vinifera*, 5–9% by wt. of an extract from *Feronia elephantum*, 8–11% by wt. of an extract from *Punica grantum*, 4–9% by wt. of an extract from *Ziniber officnale*, 2–11% by wt. of an extract from *Piper nigrum*, 8–12% by wt. of an extract from *Piper longum* and 2–11% by wt. of an extract from *Azadirachta indica* to a fine paste and mixing them with one or more pharmaceutically acceptable additives/carriers.

In another embodiment of the present invention, the extract is an aqueous extract.

In still another embodiment of the present invention, the plant part of *Aegle marmelos, Withania somnifra* and *Blechnum orintale* is root.

In yet another embodiment of the present invention, the plant part of *Vitis vinifera, Feronia elephantum, Piper nigrum* and *Piper longum* is fruit.

In one more embodiment of the present invention, the plant part of *Punica grantum* is fruit rind.

In one another embodiment of the present invention, the plant part of *Ziniber officnale* is rhizome.

In an embodiment of the present invention, the plant part of *Azadirachta indica* is bark.

In accordance with the third object of the present invention, there is provided a method of treating gastric ulcer in a subject, said method comprises administering an effective amount of the synergistic herbal composition essentially comprises 4–10% by wt. of an extract from *Aegle marmelos* and 4–11% by wt. of an extract from *Withania somnifra* and optionally comprises 5–8% by wt. of an extract from *Blechnum orintale*, 5–11% by wt. of an extract from *Vitis vinifera*, 5–9% by wt. of an extract from *Feronia elephantum*, 8–11% by wt. of an extract from *Punica grantum*, 4–9% by wt. of an extract from *Ziniber officnale*, 2–11% by wt. of an extract from *Piper nigrum*, 8–12% by wt. of an extract from *Piper longum* and 2–11% by wt. of an extract from *Azadirachta indica* along with one or more pharmaceutically acceptable additives/carriers.

In an embodiment of the present invention, the subject is a mammal including human being.

In another embodiment of the present invention, 50 to 100 mg of the composition is administered per Kg of body weight to the subject.

In yet another embodiment of the present invention, the composition can be in the form of tablets, capsules, syrup or by any other form known in the art.

In still another embodiment of the present invention, the composition is administered orally, intra-muscularly, and by any other conventional methods.

In one more embodiment of the present invention, the composition may be used for therapeutic as well as prophylactic treatment of gastric ulcer.

In one another embodiment of the present invention, the subject may be administered a single bolus dose or a multiple dose.

BRIEF DESCRIPTION OF THE TABLES

In the tables accompanying the specification,

Table 1 represents the effect of Omeprazole (a standard drug) and the new herbal composition (HF) against Cold Restraint Ulcer (CRU) Model.

Table 2 compares the percentage protection of Omeprazole and the Herbal composition (HF) against Cold Restraint Ulcer (CRU) Model.

Table 3 gives the effect of Omeprazole and the Herbal composition (HF) against Aspirin induced ulcer model.

Table 4 gives the percentage protection of Omeprazole and the Herbal composition (HF) against aspirin induced ulcer model.

Table 5 gives the effect of Omeprazole and the Herbal composition (HF) against histamine induced duodenal ulcer in Guinea pig.

Table 6 gives the percentage protection of Omeprazole and the Herbal composition (HF) against histamine induced duodenal ulcer in Guinea pigs.

able 7 gives the effect of Omeprazole and the Herbal composition (HF) against Ethanol Induced Ulcer Model.

Table 8 gives the percentage protection of Omeprazole and the Herbal composition (HF) against Alcohol induced Ulcer Model.

Table 9 gives the effect of Omeprazole and the Herbal composition (HF) against pyloric ligation induced Ulcer.

Table 10 gives the percentage protection of Omeprazole and the Herbal composition (HF) against pyloric ligation induced Ulcer.

Table 11 gives the composition of the Herbal composition (HF) of the present invention.

The present invention is further described with reference to the following experiments which are given by way of illustration and therefore should not be construed to limit the scope of the invention in any manner.

EXPERIMENTAL PROTOCOL

Invivo Experiments

The Applicants have carried out several experiments under different induced ulcer conditions and the effect of the herbal composition were studied and are tabulated herebelow. The effect of the herbal composition has been compared with respect to a known anti-ulcer drug "Omeprazole".

EXPERIMENT 1

Effect on Cold Restraint Ulcers (CRU) Model
Method:
Adult rats of either sex, weighing 150–175 grams are fasted for 24 hours in metallic cages with raised mesh bottoms to prevent coprophagia and were allowed free access to water. The test drugs were administered 45 minutes before immobilizing the animals. The rats were immobilized in the restraint cage and kept at 4° C. in BOD incubator for 2 hours (According to the method of Senay and Levine 1967). The animals were sacrificed immediately after the restraint period. The abdomen was cut opened; stomach was taken out and incised along the greater curvature to observe the gastric lesions with the help of Magnascope (5× magnification)
The following arbitrary scoring system was used to grade the severity and intensity of the lesions:

1. Shedding of epithelium=10
2. Petechial and frank hemorrhages=20
3. One or two ulcers=30
4. More than two ulcers=40
5. Perforated ulcers=50

The presence of any of these lesions was considered as a positive ulcerogenic response which has been shown as percentage of rats showing gastric lesions. The severity of ulcers is expressed in terms of ulcer index, which is the mean score of gastric lesions of all the rats in a group. The term Ulcer Index is defined as:

Ulcer Index $(U.I.) = Us + Up \times 10^{-1}$ where Us=Mean severity of ulcer score and Up=Percentage of animals with Ulcer incidences
The percentage protection is calculated as follows:

Percentage protection=$(C-T/C) \times 100$.

where C=Number of animals showing ulcer response in control group and
T=Number of animals showing ulcer response in test group.

The effect of the herbal composition of the present invention hereafter referred to as "HF" against Cold Restraint Ulcer Model (CRU) is given in Table 1. The effect of the standard drug "Omeprazole" is also given in Table 1 given at the end of the description. Percentage protection of the herbal composition of the present invention (HF) and Omeprazole against CRU model are tabulated in Table 2 given at the end of the description.
Inference:
The composition of the present invention is significantly effective in CRU model.

EXPERIMENT 2

Effect on Aspirin Induced Gastric Ulcer Model
Method:
Gastric ulceration was induced by aspirin according to the method of Djahanguiri (1969). Aspirin (150 mg/Kg.) was administered per orally as a suspension in gum-acacia and the animal was sacrificed 5 hr. after the aspirin treatment and the ulcer index with protection index were calculated.

The effect of HF against aspirin induced gastric ulcer is given in Table 3. The effect of the standard drug "Omeprazole" is also given in Table 3 given at the end of the description.

Percentage protection of the herbal composition of the present invention (HF) and Omeprazole against this model are tabulated in Table 4 given at the end of the description.
Inference:
The herbal composition of the present invention is effective against Aspirin induced gastric ulcer model.

EXPERIMENT 3

Effect on Histamine Induced Ulcer Model
Method:
1. Animals were fasted for 24 hours with access to water.
2. The drug was given orally 1 hour prior to the histamine administration.
3. Histamine was administered in a dose of 0.25 mg/Kg, i.m. at 30 minutes interval for 7 times and it induced 100% duodenal ulceration in guinea pig (According to the method of Watt and Eagleton 1964).
4. The animals were sacrificed after half an hour of last injection under ether anesthesia.
5. The stomach along with duodenum were removed washed thoroughly and examined for the lesions. Ulcer index and protection index were calculated.

The effect of HF against Histamine induced duodenal ulcer is given in Table 5. The effect of the standard drug "Omeprazole" is also given in Table 5 given at the end of the description.
Percentage protection of the herbal composition of the present invention (HF) and Omeprazole against Histamine induced duodenal ulcer are tabulated in Table 6 given at the end of the description.
Inference:
The Herbal composition of the present invention "HF" shows significant anti ulcer effect against this model.

EXPERIMENT 4

Effect on Alcohol Induced Gastric Ulcers in Rats

Method:
1. Adult rats of either sex were taken; weighing 150–175 grams were fasted for 24 hours with free access to water.
2. The test drugs were administered (p.o.) 45 minutes before alcohol administration.
3. 1 ml of chilled absolute alcohol was administered (p.o.) to the rats (According to the Wittetal).
4. Immediately after 1 hour, the animals were anesthetized, abdomen was cut opened stomach was taken out and incised along the greater curvature to observe the gastric lesions.
   The ulcers are examined under the 5× magnification with the help of magnascope.
   Absolute ethanol lesions appears as blackish lesions grouped in patches of varying size, usually parallel to the major axis of the stomach.
5. The lengths of the lesions are measured and summated to give a total lesion score, then calculated and expressed in percentage.

The effect of HF against alcohol induced ulcer model is given in Table 7. The effect of the standard drug "Omeprazole" is also given in Table 7 given at the end of the description.

Percentage protection of the herbal composition of the present invention (HF) and Omeprazole against alcohol induced ulcer model are tabulated in Table 8 given at the end of the description.

Inference:
The composition of the present invention does not show any significant effect against alcohol induced gastric ulcer model.

EXPERIMENT 5

Effect on Pyloric Ligation Induced Ulcer Model

Method:
1. Animals were fasted for 24 hours in the raised mesh bottom cages to prevent coprophagia and were allowed free access to water.
2. The control group of rats was feed with the vehicle and the experimental groups with their respective drugs 45 minutes prior to the ligation.
3. The animal was anesthetized, abdomen was cut opened under xiphoid process, and the pyloric portion of the stomach was slightly lifted and ligated avoiding any damage to the adjacent blood vessels (According to the method of Shay et al. 1945).
4. The animals were stitched and kept for 4 hours with free access to water.
5. After 4 hours the animals were sacrificed under ether anesthesia and the stomach was dissected out incised along the greater curvature.
6. The stomach was washed thoroughly and the ulcer index was scored as per in other ulcer models.

The effect of HF against pyloric ligation induced ulcer is given in Table 9. The effect of the standard drug "Omeprazole" is also given in Table 9 given at the end of the description. Percentage protection of the herbal composition of the present invention (HF) and Omeprazole against pyloric ligation induced ulcer are tabulated in Table 10 given at the end of the description.

Inference:
On comparison, Herbal composition shows high anti ulcer activity. The anti ulcer activity of the herbal composition is higher than that of Omeprazole.

EXPERIMENT 6

Herbs and Preparation of the Composition

Method:
For the purpose of conducting animal experiment all the herbs are washed dried and pulverized. All the herbs are taken in the proportion as shown in Table 11. To this water was added and boiled and concentrated to appropriate consistency. The components and their proportions of the standard "herbal composition" (HF) according to one embodiment of the present invention are listed in Table 11 given at the end of the description. The parts of the herbs which can be used is also mentioned. The placebo preparation is designed to taste, smell and look like an Ayurvedic herbal formulation.

TABLE 1

Effect of New herbal composition (HF) against Cold Restraint Ulcer Model (CRU) with Omeprazole as a standard drug.

| Compound and Doses | Ulcer severity_(type of lesions) Scores (No. of rats showing lesions/No. of rats tested) | | | | | Mean severity of ulcer score | Percentage of ulcer incidence (No. of rats showing ulcer/ total No. of rats used) | Ulcer index | Protection index |
|---|---|---|---|---|---|---|---|---|---|
| | 10 | 20 | 30 | 40 | 50 | | | | |
| Control CRU | — | 6/10 | 4/10 | — | — | 24 | 100 (10/10) | 12.4 | 00 |
| CRU + HF (50 mg/Kg, p..o.) | 4/10 | 2/10 | — | — | — | 08 | 60 (6/10) | 6.8 | 45.16 |
| CRU + Omeprazole (10 mg/Kg, p.o.) | 3/10 | 2/10 | — | — | — | 07 | 50 (5/10) | 5.7 | 54.03 |

In the table, 10 = Shedding of epithelium; 20 = Petechial and frank hemorrhages; 30 = One or two ulcers; 40 = More than two ulcers; 50 = Perforated ulcers.

TABLE 2

Percentage protection of Herbal composition against Cold Restraint Ulcer Model (CRU) taking Omeprazole as a standard drug.

| GROUP | PERCENTAGE PROTECTION |
|---|---|
| Herbal composition (HF) of the present invention (50 mg/Kg) | 83.58 |
| *Omerprazole (10 mg/Kg) | 100% |

*The protection of Omeprazole was taken as 100% as it was the standard compound and the percentage protections of other compounds are in respect to the protection of Omeprazole.

TABLE 3

Effect of Herbal composition against Aspirin induced ulcer model with Omeprazole as a standard drug.

| Compound and Doses | Ulcer severity (type of lesions) Scores (No. of rats showing lesions/No. of rats tested) | | | | | Mean severity of ulcer score | Percentage of ulcer incidence (No. of rats showing ulcer/total No. of rats used) | Ulcer index | Protection index |
|---|---|---|---|---|---|---|---|---|---|
| | 10 | 20 | 30 | 40 | 50 | | | | |
| Control Aspirin (150 mg/Kg, p.o.) | — | 2/6 | 4/6 | — | — | 26.6 | 100 (6/6) | 12.66 | 00 |
| Aspirin + Herbal composition (100 mg/Kg) | 2/6 | 3/6 | — | — | — | 13.3 | 83.3 (5/6) | 9.66 | 23.69 |
| Aspirin + Omeprazole (20 mg/Kg) | 2/6 | 1/6 | — | — | — | 6.6 | 50 (3/6) | 5.66 | 54.81 |

In the table, 10 = Shedding of epithelium; 20 = Petechial and frank hemorrhages; 30 = One or two ulcers; 40 = More than two ulcers; 50 = Perforated ulcers.

TABLE 4

Percentage protection of Herbal composition against aspirin induced ulcer model taking Omeprazole as a standard drug.

| Compound | Percentage protection |
|---|---|
| Herbal composition (50 mg/Kg) | 60.12 |
| *Omeprazole (10 mg/Kg) | 100 |

*The protection of Omeprazole was taken as 100% as it was the standard compound and the percentage protections of other compounds are in respect to the protection of Omeprazole.

TABLE 5

Effect of Herbal composition against histamine induced duodenal ulcer in Guinea pig with Omeprazole as a standard drug

| Groups and doses of compounds | Ulcer severity (type of lesions) Score (No. Guinea pig showing lesions/No. Guinea pig tested) | | | | | Mean severity of ulcer score | Percentage of ulcer incidence (No. of animals showing ulcer/total No. of animals used) | Ulcer index | % Protection | Volume of gastric fluid (mL) |
|---|---|---|---|---|---|---|---|---|---|---|
| | 10 | 20 | 30 | 40 | 50 | | | | | |
| Ulcer Control (Histamine (25 mg/Kg, i.m.) | — | — | 1/3 | 2/3 | — | 36.6 | 100 (3/3) | 13.66 | 00 | 4.33 ± 1.1 |

TABLE 5-continued

Effect of Herbal composition against histamine induced duodenal ulcer in Guinea pig with Omeprazole as a standard drug

| Groups and doses of compounds | Ulcer severity (type of lesions) Score (No. Guinea pig showing lesions/ No. Guinea pig tested) | | | | | Mean severity of ulcer score | Percentage of ulcer incidence (No. of animals showing ulcer/total No. of animals used) | Ulcer index | % Protection | Volume of gastric fluid (mL) |
|---|---|---|---|---|---|---|---|---|---|---|
| | 10 | 20 | 30 | 40 | 50 | | | | | |
| Histamine + HF (50 mg/Kg., p.o.) | — | — | — | 1/3 | — | 13.33 | 33.3 (1/3) | 4.66 | 65.88 | 2.7 ± 0.37 |
| Histamine + Omeprazole (10 mg/Kg, p.o.) | — | 1/3 | — | — | — | 6.66 | 33.33 (1/3) | 3.99 | 70.79 | 1.0 ± 0.2 |

TABLE 6

Percentage protection of Herbal composition against histamine induced duodenal ulcer in Guinea pig taking Omerprazole as a standard drug.

| COMPOUND | PERCENTAGE PROTECTION |
|---|---|
| Herbal composition | 93.07 |
| *Omeprazole | 100 |

*The protection of Omeprazole was taken as 100% as it was the standard compound and the percentage protections of other compounds are in respect to the protection of Omeprazole.

TABLE 7

Effect of Herbal composition against Ethanol Induced Ulcer Model with Omeprazole as a standard drug.

| COMPOUND | LENGTH OF HEMORRHAGIC BANDS (mm ± SE) |
|---|---|
| Ethanol Control | 73.5 ± 1.5 |
| Herbal composition (HF) of the present invention (100 mg/Kg, p.o.) + Ethanol | 69.0 ± 7.0 |
| Omeprazole (100 mg/Kg, p.o.) + Ethanol | 56.0 ± 9.12 |

TABLE 8

Percentage protection of Herbal composition against Alcohol induced Ulcer Model taking Omeprazole as a standard drug.

| COMPOUNDS | PROTECTION |
|---|---|
| Herbal composition | 25.71 |
| *Omerprazole | 100.0 |

*The protection of omeprazole was taken as 100% as it was the standard compound and the percentage protections of other compounds are in respect to the protection of omeprazole.

TABLE 9

Effect of Herbal composition against pyloric ligation induced Ulcer taking Omeprazole as a Standard drug

| Groups | Ulcer Index | Protection Index |
|---|---|---|
| Ligation Control | 16.6 | 00 |
| Ligation + Herbal composition (50 mg/Kg, p.o.) | 4.2 | 65.89 |
| Ligation + Omeprazole (10 mg/Kg, p.o.) | 6.6 | 51.44 |

TABLE 10

Percentage protection of Herbal composition against pyloric ligation induced Ulcer Model taking Omeprazole as a standard drug.

| COMPOUNDS | PROTECTION |
|---|---|
| Herbal composition | 124.0 |
| *Omeprazole | 100 |

*The protection of Omeprazole was taken as 100% as it was the standard compound and the percentage protections of other compounds are in respect to the protection of Omeprazole.

TABLE 11

Composition of the Herbal composition (HF) of the present invention.

| S. NO. | NAME OF THE INGREDIENT (PART USED) | % |
|---|---|---|
| 1 | *Blechnum orintale* (root) | 5–6% |
| 2 | *Vitis vinifera* (Fruit) | 5–9% |
| 3 | *Aegle marmelos* (Root) | 4–7% |
| 4 | *Withania somnifra* (Root) | 4–8% |
| 5 | *Feronia elephantum* (Fruit) | 5–8% |
| 6 | *Punica grantum* (Fruit) | 8–10% |
| 7 | *Ziniber officnale* (Rhizome) | 4–8% |
| 8 | *Piper nigrum* (Fruit) | 2–9% |
| 9 | *Piper longum* (Fruit) | 8–10% |
| 10 | *Azadirachta indica* (Bark) | 2–9% |

What is claimed is:

1. A composition comprising an extract obtained from the plant parts of *Aegle marmelos* and *Withania somnifra* and from the plant parts of at least one member selected from the group consisting of *Blechnum orientate, Vitis vinifera, Feronia elephantum, Punica granatum, Zingiber officinale, Piper nigrum, Piper longum* and *Azadirachta indica* and optionally with one or more pharmaceutically acceptable additive(s) or carrier(s) wherein the composition comprises:

4–10% by wt. of an extract from *Aegle marmelos* and 4–11% by wt. of an extract from *Withania somnifra* and further comprises at least one of 5–8% by wt. of an extract from *Blechnum orientale*, 5–11% by wt. of an extract from *Vitis vinifera*, 5–9% by wt. of an extract from *Feronia elephantum*, 8–11% by wt. of an extract from *Punica granatum*, 4–9% by wt. of an extract from *Zingiber officinale*, 2–11% by wt. of an extract from *Piper nigrum*, 8–12% by wt. of an extract from *Piper longum* and 2–11% by wt. of an extract from *Azadirachta indica* and optionally with one or more pharmaceutically acceptable additive(s) or carrier(s).

2. A composition as claimed in claim 1, wherein the extract is an aqueous extract.

3. A composition as claimed in claim 1, wherein the plant part of *Aegle marmelos, Withania somnifra* and *Blechnum orintale* is a root.

4. A composition as claimed in claim 1, wherein the plant part of *Vitis vinifera, Feronia elephantum, Piper nigrum* and *Piper longum* is a fruit.

5. A composition as claimed in claim 1, wherein the plant part of *Punica grantum* is a fruit rind.

6. A composition as claimed in claim 1, wherein the plant part of *Ziniber officnale* is a rhizome.

7. A composition as claimed in claim 1, wherein the plant part of *Azadirachta indica* is a bark.

8. A process for the preparation of a composition, said process comprising:

obtaining an extract from the plant parts of *Aegle marmelos* and *Withania somnifra* and from the plant parts of at least one member selected from the group consisting of *Blechnum orientale, Vitis vinifera, Feronia elephantum, Punica granatum, Zingiber officinale, Piper nigrum, Piper longum* and *Azadirachta indica* and, optionally mixing the extract(s) with one or more pharmaceutically acceptable additive(s) or carrier(s) combining:

4–10% by wt. of an extract from *Aegle marmelos* and 4–11% by wt. of an extract from *Withania somnifra* and mixing said extracts with at least one of 5–8% by wt. of an extract from *Blechnum orientale*, 5–11% by wt. of an extract from *Vitis vinifera*, 5–9% by wt. of an extract from *Feronia elephantum*, 8–11% by wt. of an extract from *Punica granatum*, 4–9% by wt. of an extract from *Zingiber officinale*, 2–11% by wt. of an extract from *Piper nigrum*, 8–12% by wt. of an extract from *Piper longum* and 2–11% by wt. of an extract from *Azadirachta indica* and optionally mixing the extract(s) with one or more pharmaceutically acceptable additive(s) or carrier(s).

9. A process as claimed in claim 8, wherein the extract is an aqueous extract.

10. A process as claimed in claim 8, wherein the plant part of *Aegle marmelos, Withania somnifra* and *Blechnum orintale* is a root.

11. A process as claimed in claim 8, wherein the plant part of *Vitis vinifera, Feronia elephantum, Piper nigrum* and *Piper longum* is a fruit.

12. A process as claimed in claim 8, wherein the plant part of *Punica grantum* is a fruit rind.

13. A process as claimed in claim 8, wherein the plant part of *Ziniber officnale* is a rhizome.

14. A process as claimed claim 8, in the plant part of *Azadirachta indica* is a bark.

15. A composition for the treatment of gastric ulcer, said composition comprising an extract obtained from the plant parts of *Aegle marmelos* and *Withania somnifra* and from the plant parts of at least one member selected from the group consisting of *Blechnum orientale, Vitis vinifera, Feronia elephantum, Punica granatum, Zingiber officinale, Piper nigrum, Piper longum* and *Azadirachta indica* and optionally with one or more pharmaceutically acceptable additive (s) or carrier(s) wherein the composition comprises:

4–10% by wt. of an extract from *Aegle marmelos* and 4–11% by wt. of an extract from *Withania somnifra* and further comprises at least one of an extract from *Blechnum orientale*, an extract from *Vitis vinifera*, an extract from *Feronia elephantum*, an extract from *Punica granatum*, an extract from *Zingiber officinale*, an extract from *Piper nigrum*, an extract from *Piper longum* and an extract from *Azadirachta indica* and optionally with one or more pharmaceutically acceptable additive(s) or carrier(s).

\* \* \* \* \*